US00PP26575P2

(12) United States Plant Patent
Bron

(10) Patent No.: US PP26,575 P2
(45) Date of Patent: Apr. 5, 2016

(54) ***POPULUS* TREE NAMED 'PRAIRIE SKYRISE'**

(50) Latin Name: *Populus tremuloides*
Varietal Denomination: Prairie Skyrise

(71) Applicant: Vince A. Bron, Grand Forks (CA)

(72) Inventor: Vince A. Bron, Grand Forks (CA)

( * ) Notice: Subject to any disclaimer, the term of this patent is extended or adjusted under 35 U.S.C. 154(b) by 137 days.

(21) Appl. No.: 13/998,650

(22) Filed: Nov. 20, 2013

(51) Int. Cl.
*A01H 5/00* (2006.01)

(52) U.S. Cl.
USPC ..... Plt./218

(58) Field of Classification Search
USPC ..... Plt./218
See application file for complete search history.

*Primary Examiner* — Keith Robinson
(74) *Attorney, Agent, or Firm* — Penny J. Aguirre

(57) ABSTRACT

A new cultivar of *Populus* tree, 'Prairie Skyrise', that is characterized by its fastigate plant habit, its very dense and compact branching habit, its very vigorous growth rate, and its tendency to break dormancy early with bright green new growth.

2 Drawing Sheets

Genus/species: *Populus tremuloides*.
Varietal denomination: 'Prairie Skyrise'.

BACKGROUND OF THE INVENTION

The present invention relates to a new and distinct cultivar of *Populus tremuloides* and will be referred to hereafter by its cultivar name, 'Prairie Skyrise'. 'Prairie Skyrise' represents a new cultivar of aspen, a deciduous tree grown for landscape use.

The Inventor discovered the new cultivar in June of 2010 as a naturally occurring whole plant mutation of *Populus tremuloides*. The new cultivar was discovered in a production block that was planted with seeds of unnamed plants of *Populus tremuloides* at a nursery in Grand Forks, British Colombia, Canada.

Asexual propagation of the new cultivar was first accomplished by tissue culture by the Inventor in Kelowna, British Columbia, Canada in June 2010. Asexual propagation by tissue culture of the new cultivar has shown that the unique characteristics of the new cultivar are stable and reproduced true to type in successive generations.

SUMMARY OF THE INVENTION

The following traits have been repeatedly observed and represent the characteristics of the new *Populus*. These attributes in combination distinguish 'Prairie Skyrise' as a unique and distinct cultivar of *Populus*.

1. 'Prairie Skyrise' exhibits a fastigate plant habit.
2. 'Prairie Skyrise' exhibits a very dense and compact branching habit.
3. 'Prairie Skyrise' exhibits a very vigorous growth rate.
4. 'Prairie Skyrise' exhibits a tendency to break dormancy early with bright green new growth.

Typical plants of the parent species *Populus tremuloides*, differs from 'Prairie Skyrise' in having a plant habit that is less compact (40 percent fewer buds per one-year old branch) with less dense branching and more spreading (not fastigate) and in having more rounded leaves. 'Prairie Skyrise' can also be compared to the *Populus tremula* cultivar 'Erecta' (not patented) and the *Populus×canescens* cultivar 'Tower' (not patented). 'Erecta' is similar to 'Prairie Skyrise' in having a similar size and fastigate plant habit. 'Erecta' differs from 'Prairie Skyrise' in having a plant habit that is less compact (40 percent fewer buds per one-year old branch), with less dense branching, in having a slower growth rate, in having new foliage that is red in color, and in breaking dormancy later. 'Tower' is similar to 'Prairie Skyrise' in having a vigorous growth rate and in having a columnar form. 'Tower' differs from 'Prairie Skyrise' in having a plant habit that is less narrow, less compact with less dense branching and in having leaves that are larger in size.

BRIEF DESCRIPTION OF THE DRAWINGS

The accompanying colored photographs illustrate the overall appearance and distinct characteristics of the new *Populus*. The photographs were taken of two year-old plants of 'Prairie Skyrise' as grown outdoors in 29.9-liter containers in Grand Forks, British Columbia, Canada.

The photograph in FIG. 1 provides a view of the plant habit of 'Prairie Skyrise' in summer.

Figure 1:
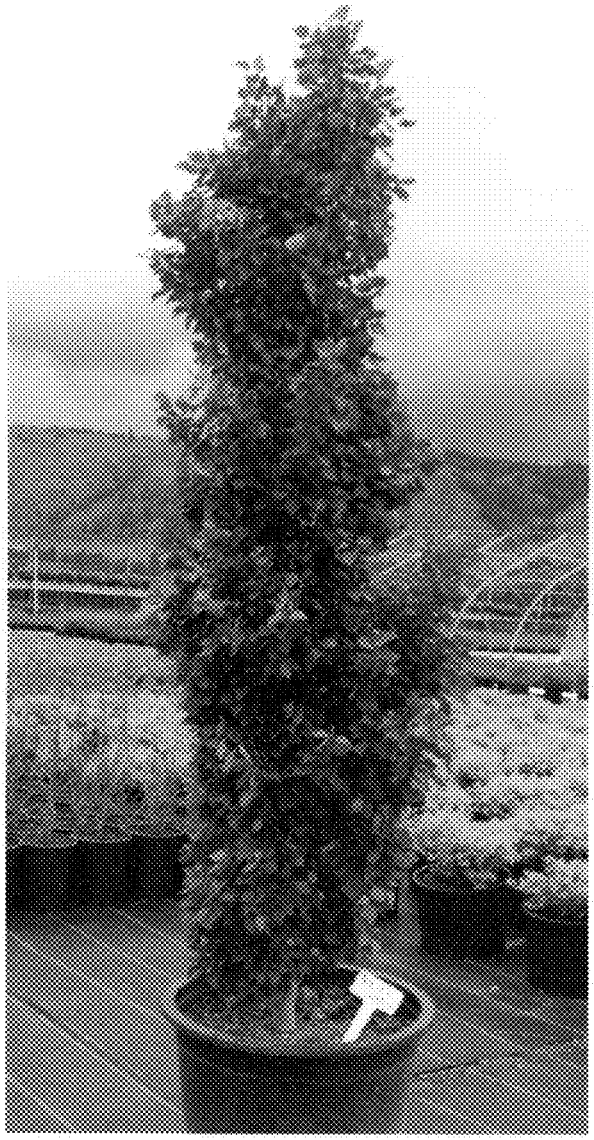
Figure 2:
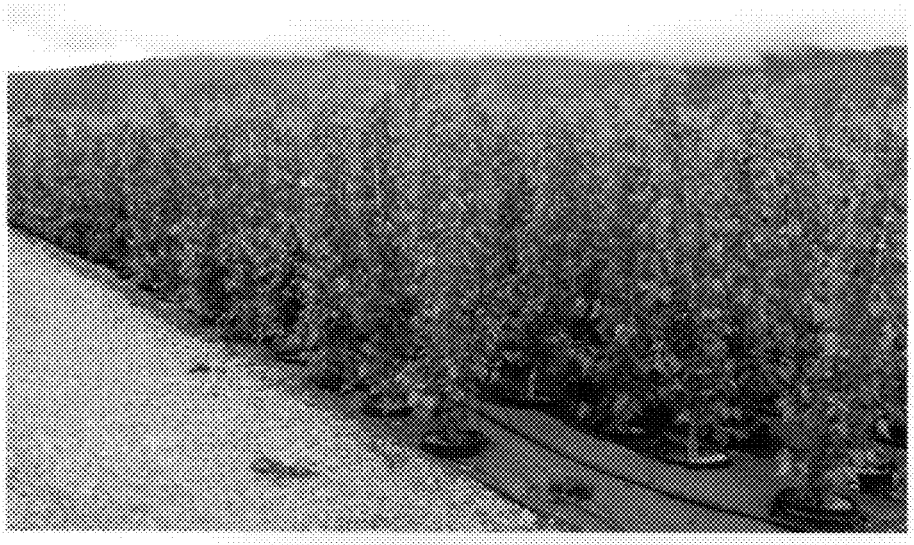

The photograph in FIG. 2 provides a view of a container block of 'Prairie Skyrise'.

Figure 3:
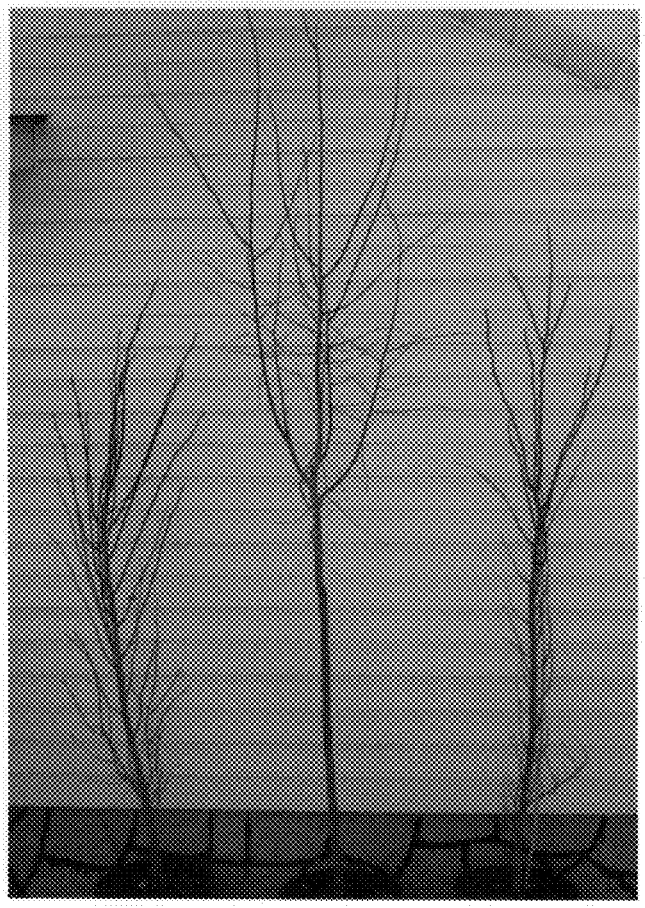

The photograph in FIG. 3 was taken in winter and provides a view of the branching habit of 'Prairie Skyrise' (left), *Populus tremuloides* (middle), and 'Erecta' (right).

The colors in the photographs are as close as possible with the digital photography and printing techniques utilized and the color codes in the detailed botanical description accurately describe the colors of the new *Populus*.

BOTANICAL DESCRIPTION OF THE PLANT

The following is a detailed description of two year-old plants of the new cultivar as grown outdoors in 29.9-liter containers in Grand Forks, British Columbia, Canada. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant type*.—Deciduous tree.

*Plant habit*.—Fastigate.

*Height and spread*.—An average of 2.2 m height and 44 cm in spread.

*Hardiness*.—At least U.S.D.A. Zones 1 to 5.

*Diseases*.—No particular susceptibility or resistance has been observed.

*Root description*.—Fibrous and fine roots spread laterally, N200D in color.

*Root development*.—An average of 30 days for root initiation with a rooted cutting produced after an average of three months.

*Growth rate*.—Very vigorous.

Branch description:

*Trunk size*.—Average of 3.3 cm diameter measured 30 cm from soil line.

*Stem color*.—New growth (shoots) in-between 166A and 166B, old growth twigs N200B with lenticels 179D, bark (trunk) 198B to 198D suffused with 189C, lenticels 175A.

*Stem shape*.—Rounded.

*Stem size*.—Main stems; average of 1.1 cm in diameter and 80 cm in length (including peduncle), lateral branches; average of 3 mm in diameter and 10 cm in length.

*Stem surface*.—New growth; glabrous, glaucescent, old growth (trunk); glabrous, slightly lenticellate, lenticels; linear in shape and an average of 2.5 mm in length.

*Branching*.—Densely branched; an average of 6 lateral branches per main branch, branches are held at an average angle of 20° from vertical.

*Buds*.—An average of 8 mm in length and 3 mm in width, color; 183A, apex is 166A, shape; ovoid, apex; pointed, surface; glabrous, an average 14 per 30 cm on a 1-year old branch taken from the center of the tree.

*Internode length*.—Main stems; an average of 13 cm, lateral stems; an average of 4.0 cm.

Foliage description:

*Leaf shape*.—Ovate.

*Leaf division*.—Simple.

*Leaf base*.—Cordate.

*Leaf apex*.—Cuspidate.

*Leaf venation*.—Pinnate, color on mature foliage upper and lower leaf surface; a blend of N137A and 139A.

*Leaf margin*.—Serrate and sinuate.

*Leaf attachment*.—Petiolate.

*Leaf arrangement*.—Alternate.

*Leaf attitude*.—Held relatively flat at an average angle of 55° from vertical.

*Leaf surface*.—Glabrous on upper and lower surfaces, moderately rugose on upper surface.

*Leaf size*.—An average of 9.5 cm in length and 7.0 cm in width.

*Leaf internode length*.—An average of 3.5 cm.

*Leaf color*.—New growth upper and lower surface; 144B, mature foliage upper and lower surface; a blend of N137A and 139A, fall foliage upper surface; a blend of 14A to 14B and 191A, fall foliage lower surface; a blend of 160B and 162B.

*Petioles*.—An average of 2.4 cm in length and 1.5 mm in width, flattened shape, 182A in color, surface glabrous.

Flower description: Flowering has not been observed for the new cultivar.

It is claimed:

1. A new and distinct cultivar of *Populus* tree named 'Prairie Skyrise' as herein illustrated and described.

* * * * *